United States Patent [19]
Okabe

[11] Patent Number: 5,628,729
[45] Date of Patent: May 13, 1997

[54] INTERFACE FOR IONTOPHORESIS WITH HYDRATING MECHANISM

[75] Inventor: Keiichiro Okabe, Tokyo, Japan

[73] Assignee: Hisamitsu Pharmaceuticals Co., Inc., Tosu, Japan

[21] Appl. No.: 361,459

[22] Filed: Dec. 21, 1994

Related U.S. Application Data

[63] Continuation of Ser. No. 13,093, Feb. 3, 1993, abandoned.

[30] Foreign Application Priority Data

May 27, 1992 [JP] Japan .................. 4-158939

[51] Int. Cl.$^6$ .................................................. A61N 1/30
[52] U.S. Cl. .................................................. 604/20; 607/153
[58] Field of Search ............... 604/20, 21; 607/149–152, 607/115

[56] References Cited

U.S. PATENT DOCUMENTS

| | | | |
|---|---|---|---|
| 4,166,457 | 9/1979 | Jacobsen et al. | 604/20 |
| 4,474,570 | 10/1984 | Ariura et al. | 604/20 |
| 4,842,577 | 6/1989 | Konno et al. | 604/20 |
| 5,032,110 | 7/1991 | Watanabe | 604/20 |
| 5,047,028 | 9/1991 | Qian | 606/49 |
| 5,084,006 | 1/1992 | Lew et al. | 604/20 |
| 5,087,241 | 2/1992 | Mathiesen et al. | 604/20 |
| 5,087,242 | 2/1992 | Petelenz et al. | 604/20 |
| 5,147,297 | 9/1992 | Myers et al. | 604/20 |
| 5,156,591 | 10/1992 | Gross et al. | 604/20 |
| 5,158,537 | 10/1992 | Haak et al. | 604/20 |

FOREIGN PATENT DOCUMENTS

417290  3/1991  Japan ...................... 604/20

*Primary Examiner*—Mark Bockelman
*Attorney, Agent, or Firm*—Foley & Lardner

[57] ABSTRACT

An interface composed of an aqueous solution supply portion capable of providing a fine hole for supplying an aqueous solution, a water-permeable electrode, and a water-absorbable or water-permeable film-like membrane, laminated integrally, wherein the fine hole for supplying the solution is made in the aqueous solution supply portion at the time of use, the aqueous solution is supplied through the water-permeable electrode and water-absorbable or water-permeable film-like membrane, and, when the aqueous solution reaches them, the drug or the drug-containing water-soluble layer dissolve and a locally high concentration solution of the drug is formed.

6 Claims, 3 Drawing Sheets

INTERFACE FOR IONTOPHORESIS WITH HYDRATING MECHANISM

This application is a continuation of application Ser. No. 08/013,093, filed Feb. 3, 1993 now abandoned.

BACKGROUND OF THE INVENTION

1. Field of the Invention

The present invention relates to an interface (or a skin contact structure) for iontophoresis.

2. Description of the Related Art

An interface for iontophoresis has a structure comprised of an assembly of a reservoir for holding a drug solution and an electrode for current dispersion.

The structure of the above-mentioned reservoir must be one which allows a predetermined amount of the drug solution to reliably reach the interface with the skin of the living body along with the elapse of time, but the reservoir itself is steric and further contains water as the medium and thus there is dilution of the drug and, further, leakage of the drug solution, water etc. to outside the interface, including the reservoir, causing leaks across the electrodes. A satisfactory structure has not yet been proposed.

SUMMARY OF THE INVENTION

Accordingly, the objects of the present invention are to eliminate the above-mentioned disadvantageous of the conventional interfaces and to provide an interface having a structure capable of accurately administering a drug, suitable for iontophoresis.

Other objects and advantages of the present invention will be apparent from the following description.

In accordance with the present invention, there is provided an interface for iontophoresis comprising an aqueous solution supplying portion capable of providing a fine hole for supplying an aqueous solution at least when used, a water-permeable electrode, and a water-absorbable or water-permeable film-like membrane laminated integrally.

BRIEF DESCRIPTION OF THE DRAWINGS

The present invention will be better understood from the description set forth below with reference to the accompanying drawings, wherein.

DESCRIPTION OF THE PREFERRED EMBODIMENTS

Figure 1:
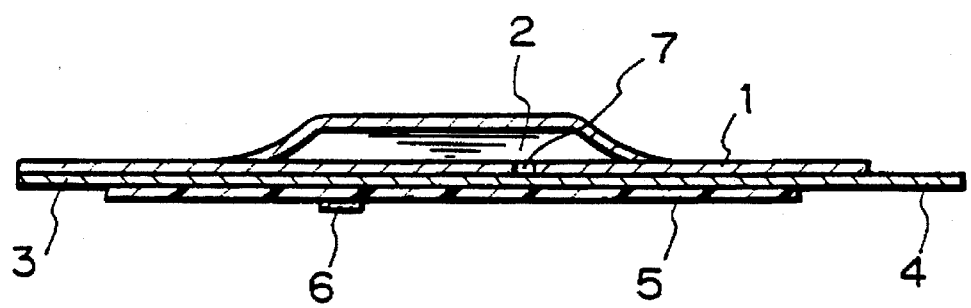
FIG. 1 is a cross-sectional view showing an embodiment of the present invention.
Figure 2:
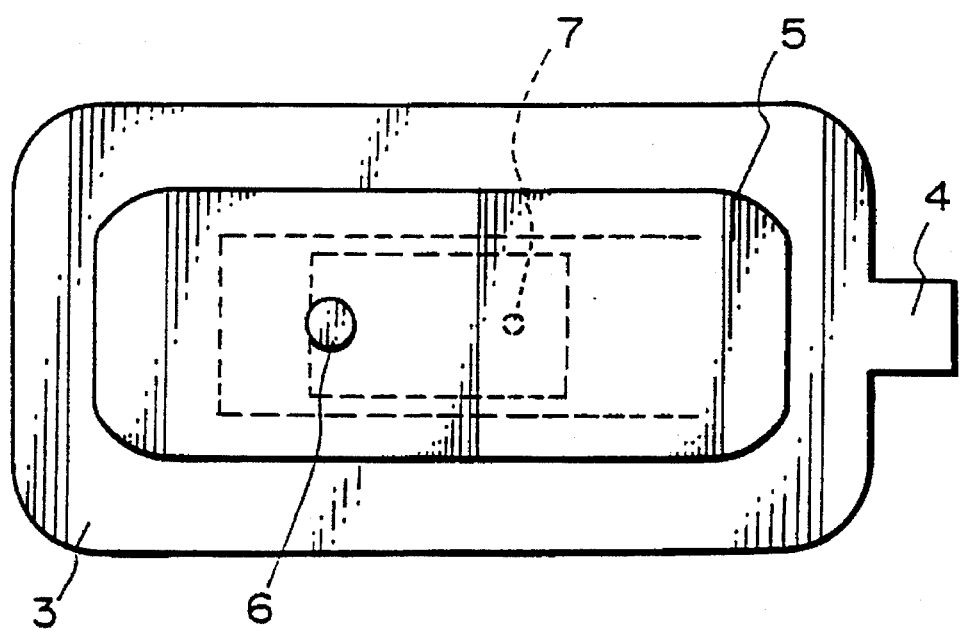
FIG. 2 is a view showing the reverse side of the embodiment shown in FIG. 1.

The characteristics of the present invention will now be explained.

As defined above, the present invention comprises an aqueous solution supplying portion capable of providing one or more fine holes for supplying an aqueous solution at least when used, a water-absorbable or water-permeable electrode, and a water-permeable film-like membrane laminated integrally. When fine holes for supplying the solution are made in the aqueous solution supplying portion at the time of use and the aqueous solution is supplied through the water-permeable electrode and water-absorbable or water-permeable film-like membrane and reaches them, the drug or the drug-containing water-soluble layer is dissolved and a locally high concentration solution of the drug is formed. Therefore, when an electric current is passed, the transdermic or transmucosal administration of the drug is promoted, while keeping the drug at a high concentration without diffusion or dilution of the drug solution.

Further, the drug solution or aqueous solution passes from the reservoir through the fine holes and gradually permeates to the water-absorbing or water-permeable film-like membrane to just fill the same, so that the solution does not leak outside.

In the present invention, it is possible to keep the drug in a solid form, that is, a dried form, before use, so that the drug is suitably stored for a long-term intact on the shelf.

Further, the drug need only be deposited on the water-absorbable or water-permeable film-like membrane in a suitable amount at a suitable time, so that effective administration of the drug becomes possible.

The aqueous solution supply portion means a combination of a sheet composed of a plastic resin (e.g., PET (polyethylene telephthalate), EVA (ethylene vinyl acetate), PE (Polyethylene), VC (vinylchloride) etc., having both softness and hardness and a reservoir composed of an ampule, container, pouch, bag, etc. in which an aqueous solution is sealed. As the sheet and the reservoir, mention may be made of ones which are formed integrally in advance or ones which are joined at the time of use.

The aqueous solution may be any one which is capable of dissolving a drug.

As a water-permeable electrode, mention may be made of a sheet or film formed partially or entirely in a meshed or porous form and having conductivity. As the raw material therefor, mention may be made of a sheet composed of carbon, silver, silver chloride, titanium, etc., a composite sheet composed of a nonwoven fabric on which carbon, silver, silver chloride, or titanium paste is printed, etc. Further, the water permeability need only be manifested at the time of use and it is not necessarily required that the above-mentioned shape be provided.

As the water-absorbable or water-permeable film-like membrane it is possible to use a layer composed of a water-permeable fiber such as a laminated membrane filter, paper, nonwoven fabric, porous film (made of, for example, nylon membrane Biodyne A®, Biodyne Plus®, cellulose ester membrane or cellulose acetate membrane etc. or the like, a water-soluble polymer (e.g., PVA (polyvinyl alcohol), soluble starch CMC (carboxymethyl cellulose), MC (methyl cellulose), hydroxypropyl cellulose etc.) holding, adhering, or containing a predetermined drug, a PVP film, or other water-absorbing (aqueous) film. Usually, it is formed into a thin film.

The aqueous solution supplying holes are fine holes made in the reservoir of the aqueous solution supplying unit. The holes suitably have a diameter of about 0.5 mm to 2 mm. It is suitably selected in accordance with the time by which the aqueous solution inside the aqueous solution supply unit is supposed to reach the drug or the shape and materials of the water-permeable electrode and the water-absorbable or water-permeable film etc. A plurality of the holes may be formed.

EMBODIMENTS

An embodiment of the present invention will now be explained in detail with reference to FIG. 1.

In FIG. 1, (1) is an aqueous solution supply member which has a reservoir structure of an ampule, container, pouch, or the like containing an aqueous solution (2) for dissolving a drug at the time of use and forming a conductive path.

At the bottom surface of the aqueous solution supplying member (1) is adhered and affixed a meshed or porous water-permeable electrode (3). At one end of this is attached an external connecting terminal (4).

The external connecting terminal (4) is served for connecting the water-permeable electrode (3) and an external iontophoresis output unit. At the connection portion, use is made of alligator clips, screws, etc.

Further, at the bottom surface of the water-permeable electrode (3), a water-absorbable or water-permeable film-like membrane (5) is affixed.

At the surface or inside of the film-like membrane (5), there is provided a dried powdery or granular, that is, solid in advance or at the time of use, drug (6) held, adhered, or contained in the film-like membrane (5).

Reference numeral (7) is a fine hole. This is made at the time of use. The aqueous solution (2) contained in the aqueous solution supply member (1) passes through the fine hole (7) and gradually permeates to the water-permeable electrode (3) and film-like membrane (5) by capillary action, dissolves the solid drug (6), and reaches the skin surface.

Due to the action of capillary action, it is possible to make adjustments so that a suitable amount of the aqueous solution can be transported to the drug, without transporting excess moisture, and therefore, it is possible to make the drug quantitatively and further reliably reach inside the body, without excessive dilution by the aid of iontophoresis.

Another embodiment will now be explained in detail with reference to FIG. 3.

In FIG. 3, (1) is an aqueous solution supply member, which has a bag-like reservoir connected in an integrally formed manner at the approximate center. The material, like in the case of FIG. 1, is a resin or plastic having flexibility and an electrical insulation property. The reservoir is made of a similar material.

The reservoir is connected to only part of the end surface of the aqueous solution supply member (1). Reference numeral (2) represents an aqueous solution, which is filled in the reservoir of the aqueous solution supply member (1). Reference numeral (3) is a water-permeable electrode, which is formed by printing or branding a conductive ink of carbon, silver, silver chloride, titanium, etc. on the rear surface of the aqueous solution supply member (1). Reference numeral (4) is an external connecting terminal, which has conductivity and which is for connection with an external iontophoresis output unit.

The external connecting terminal (4) is connected with the water-permeable electrode (3) and projects partially out at the surface of the aqueous solution supply member (1). Reference numeral (5) is a film-like membrane, which consists of said material having water-absorbency or water-permeability. At the periphery of the film-like membrane (5) is formed an adhesive layer, which is connected with the aqueous solution supply member (1). Reference numeral (6) is a drug, which is deposited on a part of the film-like membrane (5). Reference numeral (8) is a peel-off membrane, which is formed by a paper, resin, etc. coated with silicone. Reference numeral (10) is a projection, which is formed integrally with the peel-off member (8) and further passes through the film-like membrane (5) and is connected to a part of the reservoir of the aqueous solution supply member (1).

The method of use and operation will now be explained.

Figure 3A:
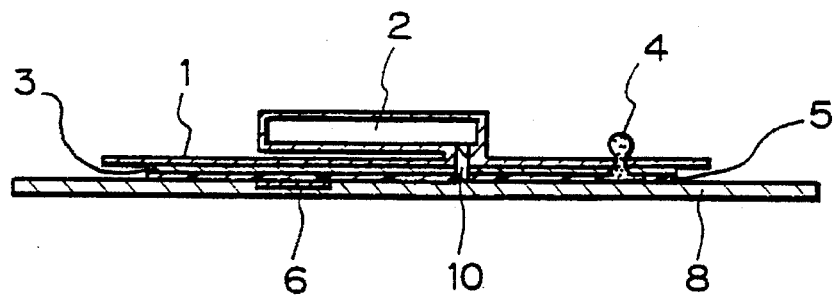
FIGS. 3(a), (b) and (c) and FIGS. 4(a), (b) and (c) are views for explaining other embodiments of the present invention.
Figure 3B:
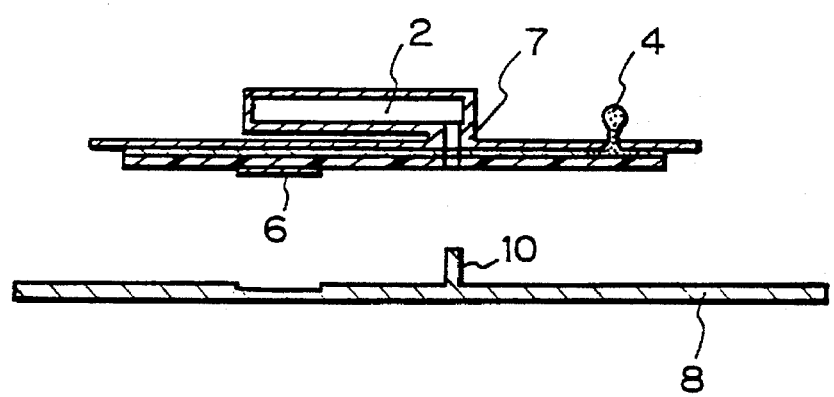

Before use, as shown in FIG. 3(a), the projection (10) of the peel-off membrane (8) and part of the reservoir of the aqueous solution supply member (1) are in a connected state. The drug (6) exists in the closed space sandwiched between the peel-off membrane (8) and the film-like membrane (5). Upon use, as shown in FIG. 3(b), the peel-off membrane (8) is peeled off. When it is peeled off, the projection (10) is pulled so as to break the connection between the reservoir of the aqueous solution supplying member (1) and the projection (10), whereby the fine hole (7) is formed.

Figure 3C:
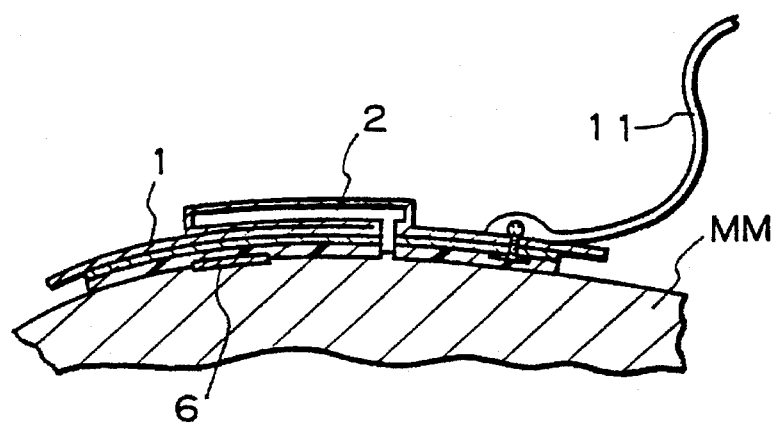

After the peel-off member (8) is peeled off, the interface is adhered to the surface of the body (MM). The state of attachment is shown in FIG. 3(c). The aqueous solution (2) inside the reservoir of the aqueous solution supplying member (1) passes through the fine hole (7) and reaches the surface of the living body (MM). At the same time, it diffuses and permeates inside the film-like membrane (5) and reaches the portion where the drug (6) is deposited.

The conductive terminal (4) and the external iontophoresis output unit are connected by the electric lead line (11) and the conductive metal fitting connected to the same. The drug (6) dissolved in the aqueous solution (2) is placed under an electrical transdermal administration state while keeping a high concentration locally.

Further, the film-like membrane (5) and the surface of the body (MM) are joined by providing an adhesive layer on the film-like membrane (5) or applying plaster from above.

Another embodiment will now be explained in detail with reference to FIG. 4.

In FIG. 4, reference numeral (12) is a reservoir, with a top surface formed by a soft member and a side surface and bottom surface formed by a hard member. Inside, the aqueous solution (2) is filled.

Reference numeral (13) is a hollow needle, which is connected to the bottom surface of the reservoir (12).

Reference numeral (14) is a supporting member, which is composed of the same material as the aqueous solution supplying member (1) explained in the previous embodiment. Reference numeral (15) is an adhesive gel which is placed around the outside periphery of the supporting member (14). The adhesive gel (15) requires only to have stickiness. Use of another adhesive agent is also possible. Reference numeral (3) is a water-permeable electrode, which consists of a nonwoven fabric on which is printed a conductive ink of carbon, silver, silver chloride, titanium, etc. Reference numeral (4) is a conductive terminal, which is formed by causing one end of the water-permeable electrode (3) to project out from the supporting member (14). Reference numeral (5) is a film-like membrane of the above-mentioned materials and structure. Reference numeral (6) is a drug, which is deposited on the bottom surface of the film-like membrane (5). Reference numeral (8) is a peel-off membrane, which is of the same materials and structure as in the embodiment shown in FIG. 3.

An explanation will now be made on the method of use and operation of this embodiment.

Figure 4A:
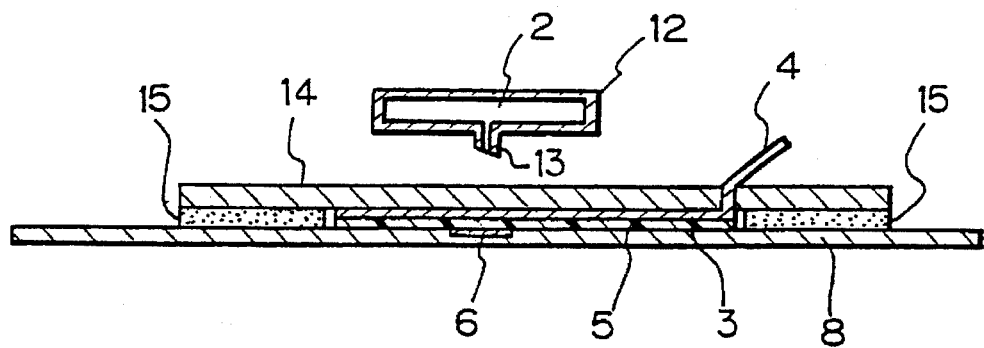
Figure 4B:
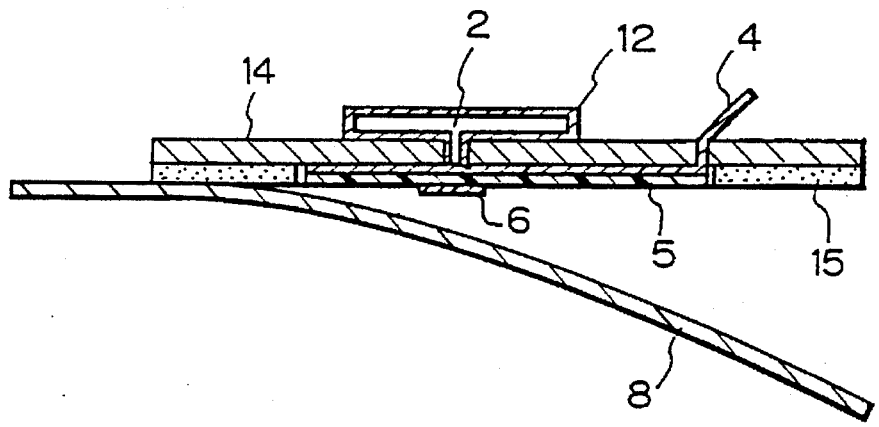
Figure 4C:
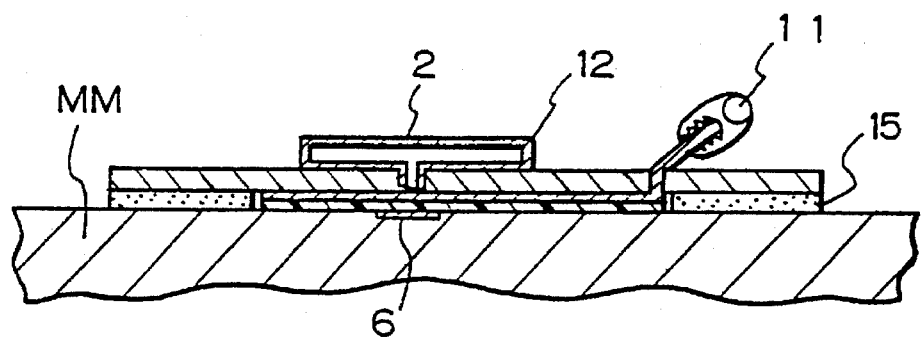

Before use, as shown in FIG. 4(a), the reservoir (12) is handled as a separate unit. The drug (6) is present in the closed space sandwiched between the film-like membrane (5) and the peel-off membrane (8). At the time of use, as shown in FIG. 4(b), the hollow needle (13) provided at the bottom surface of the reservoir (12) pierces through from the top of the supporting member (14) to reach the water-permeable electrode (3). Further, the peel-off membrane (8)

is peeled off and, as shown in FIG. 4(c), the interface is adhered to the surface of the body (MM).

By pressing the top surface of the reservoir (12) from above, the aqueous solution (2) is pushed to the outside through the hollow needle (13). Further, the aqueous solution (2) permeates through the water-permeable electrode (3) and film-like membrane (5) to reach the drug (6) and the surface of the body (MM), whereby a conductive pathway is formed between the water-permeable electrode (3) and the surface of the body (MM).

The electrical output from the external iontophoresis output unit is supplied to the water-permeable electrode (3) through the electrical lead line (11), so that the drug (6) dissolved in the aqueous solution (2) and kept at a locally high concentration is placed in an electrical transdermal administration state.

The above-mentioned three embodiments shows the case where the main electrode and the counter electrode were separate and an iontophoresis electrical output unit was provided exteriorly, but it is also possible to have an integral construction by placing the main electrode and counter electrode on the same electrically insulating member and attaching an iontophoresis electrical output unit to the same.

The above-mentioned drug is not limited in terms of its molecular weight or other physical quantities, but the interface of the present invention is particularly useful for insulin and other peptide type drugs which, despite being used in small quantities, have to be held at as high a concentration as possible and be sufficiently moist for the efficiency of the iontophoresis. Examples of the drugs are given below:

Local anesthetics: Lidocaine hydrochloride;

Antitussive expectorants: Sodium cromoglicate, ketotifen fumarate;

Bronchial vasodilators: Formoterol fumarate;

Analgesics: Nalbuphine hydrochloride, pentazocine lactate, Diclofenac sodium; Cardiacs; Dopamine hydrochloride; Psychoneurotic stabilizers: Perphenazine, phenothiazine; Antibiotics: Cefotetan disodium, dibekacin sulfate, amikacin sulfate, netilmicin sulfate, sisomicin sulfate; Anti-malignant tumor agents.

Adriamycin, mitomycin C, bleomycin hydrochloride, lentinan, picibanil, vincristine sulfate, cisplatin; Circulatory function ameliorators: Nicametate citrate, meclofenoxate hydrochloride, lisuride maleate, calcium hopantenate; Gout therapeutic agents: Allopurinol Other peptides: LHRH, enkephalin, endorphin, interferon, insulin, calcitonin, TRH, oxytocin, lypressin vasopressin, glucagon, pituitary hormones (HGH, HMG, HCG, desmopressin acetate), follicular luteinizing hormones, growth hormone releasing factors and analogues.

As mentioned in detail above, the present invention enables sufficient moisture to be supplied, without the drug solution being diluted and enables long-term storage without deteolization, decomposition, etc. since the drug is in a dried state before use. Further, since the drug is only present at the contact surface with the skin once dissolved, very highly efficient drug utilization can be achieved under electric current field with minimum leakage from the application site. Thus, this invention is particularly suitable for administration of drugs which are highly potent and very expensive.

I claim:

1. An interface for iontophoresis, comprising:
    an electrode having a first side and a second side opposite the first side, the electrode having a first opening;
    a reservoir of an aqueous solution laminated to the first side of the electrode, the reservoir having a second opening aligned with the first opening in the electrode;
    a water-supplying film laminated to the second side of the electrode and having a third opening aligned with the first and second openings;
    a medication in dry-form positioned on the water-supplying film; and
    a removable shield covering over the water-supplying film and sandwiching the medication between the shield and the water-supplying film, wherein the shield has a projection blocking at least the second opening to contain the solution in the reservoir,
    wherein the aqueous solution in the reservoir is supplied to the water-supplying film by a capillary action, which solution dissolves the medication upon removal of the shield from the water-supplying film.

2. An interface for iontophoresis as claimed in claim 1, wherein the electrode is composed of a sheet or film formed partially or entirely in a meshed or porous form and having conductivity.

3. An interface for iontophoresis as claimed in claim 1, wherein the water-supplying film is composed of a laminated membrane, paper, nonwoven fabric, porous film or water soluble polymer.

4. The interface as claimed in claim 1, wherein the first and second openings are sized just large enough to permit the aqueous solution to gradually permeate the water-supplying film without leaking.

5. The interface as claimed in claim 4, wherein the first and second openings each have a diameter of about 0.5 mm to about 2 mm.

6. The interface as claimed in claim 1, wherein the third opening is adapted to be blocked off by a surface of living tissue to prevent a leakage of the solution through the third opening.

* * * * *